United States Patent
Elias et al.

(10) Patent No.: US 9,433,787 B2
(45) Date of Patent: Sep. 6, 2016

(54) FLEXIBLE-BASE ELECTRODE ARRAY AND SURROGATE NEURAL TISSUE

(71) Applicant: The Governors of the University of Alberta, Edmonton (CA)

(72) Inventors: Anastasia Elias, Edmonton (CA); Vivian Mushahwar, Edmonton (CA); Walied Moussa, Edmonton (CA); Cheng Cheng, Edmonton (CA); Imad Khaled, Edmonton (CA); Kathryn Todd, Edmonton (CA)

(73) Assignee: The Governors of the University of Alberta, Edmonton (CA)

( * ) Notice: Subject to any disclaimer, the term of this patent is extended or adjusted under 35 U.S.C. 154(b) by 0 days.

(21) Appl. No.: 13/657,552

(22) Filed: Oct. 22, 2012

(65) Prior Publication Data
US 2013/0144369 A1 Jun. 6, 2013

Related U.S. Application Data

(60) Provisional application No. 61/550,102, filed on Oct. 21, 2011, provisional application No. 61/550,176, filed on Oct. 21, 2011.

(51) Int. Cl.
*A61N 1/05* (2006.01)
*A61N 1/36* (2006.01)
*A61B 5/00* (2006.01)
*A61B 5/04* (2006.01)

(52) U.S. Cl.
CPC ....... *A61N 1/36103* (2013.01); *A61B 5/04001* (2013.01); *A61B 5/685* (2013.01); *A61B 5/6877* (2013.01); *A61N 1/0551* (2013.01); *A61B 2562/125* (2013.01)

(58) Field of Classification Search
CPC ............ A61N 1/0526; A61N 1/0529; A61N 1/0531; A61N 1/0534; A61N 1/0551; A61N 1/36103; A61B 5/685; A61B 5/6877
USPC .................................... 607/116, 117
See application file for complete search history.

(56) References Cited

U.S. PATENT DOCUMENTS

| 6,829,498 B2* | 12/2004 | Kipke ................ A61B 5/04001 |
| | | 29/825 |
| 7,447,551 B2* | 11/2008 | Kuo et al. ..................... 607/152 |
| 8,122,596 B2* | 2/2012 | Krulevitch ........... A61N 1/0543 |
| | | 257/133 |

OTHER PUBLICATIONS

Snow et al., "Intraspinal Microstimulation using Cylindrical Multielectrodes," IEEE TBME 2006, 53(2), pp. 311-319 (Feb. 2006).
Snow et al., "Microfabricated Cylindrical Multielectrodes for Neural Stimulation," IEEE TBME 2006, 53(2), pp. 320-326 (Feb. 2006).

* cited by examiner

*Primary Examiner* — Edward Moran
*Assistant Examiner* — Michael Carey
(74) *Attorney, Agent, or Firm* — Marsh Fischmann & Breyfogle LLP; Jonathon A. Szumny

(57) ABSTRACT

A flexible-base electrode array for implantation within neural tissue, method of making the electrode array and use thereof, is provided. A surrogate neural tissue, method of making same and use thereof, is further provided. The use of the present flexible-base electrode array for implantation into the surrogate neural tissue for stimulation or recording neural activity, wherein the array is biocompatible with the surrogate tissue.

19 Claims, 17 Drawing Sheets

| Electrode Number | Individual Electrodes (no base) | Rigid-Base Array | Flexible-Base Electrode Array |
|---|---|---|---|
| 1→3 | 1.28 | 1.32 | 1.46 |
| 3→5 | 1.35 | -2.05 | 1.39 |
| 5→7 |  | 0.82 |  |
| 2→4 | 1.37 | 0.10 | 1.59 |
| 4→6 | 1.34 | -0.33 | 1.12 |
| 6→8 |  | 0.17 |  |
| Average | 1.34 | 0.004 | 1.39 |
| St.Dev | 0.03 | 1.16 | 0.20 |

FLEXIBLE-BASE ELECTRODE ARRAY AND SURROGATE NEURAL TISSUE

CROSS REFERENCE RELATED APPLICATIONS

This application claims priority of U.S. Provisional Patent Application Ser. No. 61/550,102, entitled "Surrogate Spinal Cord and Method of Making Same", filed Oct. 21, 2011 and U.S. Provisional Patent Application Ser. No. 61/550,176, entitled "Flexible-Base Electrode Array and Method of Manufacture", filed Oct. 21, 2011, both of which are incorporated herein by reference in their entireties.

TECHNICAL FIELD

A flexible-base electrode array, method of making same and use thereof is provided. An improved surrogate neural tissue (e.g. central nervous system tissue), method of making same and use thereof is provided. More specifically, the use of the present flexible-base electrode array for implantation into neural tissue such as, for example, the present surrogate neural tissue, for stimulating or recording neural activity, is provided, wherein the array provides improved biocompatibility with the neural tissue.

BACKGROUND

Central nervous system injury and disease (e.g. stroke, spinal cord injury, Parkinson's disease) affects millions of people world-wide, leaving the afflicted with significantly compromised function. For example, spinal cord injury leads to an interruption in the neural signals between the brain and the intact motor neurons below the injury site, and often causes the loss of function in organs and body parts below the level of the injury (e.g. the loss of standing, walking and sensation in the lower extremities, loss of bladder control, etc.).

Numerous strategies to restore lost neural signalling exist such as, for example, the development of implanted neuroprosthetic devices that are capable of interfacing and integrating with the nervous system to stimulate and/or record tissue activity. Intraspinal microstimulation (ISMS) is one such neuroprosthetic technique that involves the implantation of micro-sized-electrodes within the spinal cord above or below the site of injury. Electrical stimulation of the microelectrodes can overpass the interrupted neural signal and restore activation to the remaining motoneuronal pools and elements of the neural networks involved in walking, reaching, etc.

Some neuroprosthetic implants for restoring neural signalling comprise 8-12 microelectrodes individually implanted into each side of the spinal cord. The electrodes are manually positioned, allowing for flexibility of placement within the cord. However, the electrodes themselves are very fine and difficult to handle, and the process is susceptible to placement errors which can reduce the overall accuracy and efficiency of the implant.

Other neuroprosthetic implants comprise the use of arrays of electrodes that are held together by a base. The use of an array of electrodes improves the accuracy of electrode placement, but the mechanical and electrical stability of such remains unknown.

For instance, rigid, glassy polymer, ceramic or silicon base arrays such as, for example, the Utah, Mich. and Huntington Medical Research Institute (HMRI) arrays are capable of recording from or stimulating various brain regions. Such rigid arrays, however, are known to cause adverse inflammatory responses in the neural tissue with which they interface, when they are used with tissue that deforms during daily motion (e.g. elongation, bending or rotation), such as the spine. It is desirable to develop a microelectrode array capable of mechanical harmony with neural tissue, without impeding the natural deformation of the tissue during movement.

Flexible-base electrode arrays are also known such as, for example, flexible-based intracortical arrays consisting of a polyimide base. However, a polyimide base, having a modulus of elasticity of 2.97 GPa may not provide accurate mechanical and geometrical interfacing with sensitive tissues such as neural cells, the brain, and the spinal cord, which have been estimated to have an elastic modulus of between approximately 0.1 kPa to 150 MPa, depending upon the presence of absence of pia and dura mater.

One approach to improving the mechanical properties of microelectrode arrays in vivo has been to engineer devices out of biodegradable materials (e.g. polyethylene glycol) that will gradually erode upon implantation, leaving only the electrodes in place. Alternatively, bases having a bi-layer construction with a bottom layer of silicone and top layer of hydrogel are also known. Biodegradable or semi-biodegradable arrays, however, are not likely suitable for instraspinal or intracortical microstimulation/recording techniques given that the base would need to biodegrade before the patient wakes up from surgery and begins moving, and the swelling progression that is integral to the biodegradation process may disturb the electrodes themselves.

There is a need, therefore, for a flexible-base electrode array that may be suitable for accurate mechanical and geometrical interfacing with a variety of neural tissue such as, for example, spinal cord tissue. Such an array may be biocompatible with the neural tissue, capable of conforming to the surface of the tissue and undergoing similar deformation to the tissue during normal daily movement. Such an array may be used for ISMS treatment.

To date, the interaction of known microelectrode arrays with spinal cord tissue as well as their stability in the cord, particularly for long-term use, remains unknown. As such, the ability to test and develop flexible-based electrode arrays that are mechanically biocompatible with various types of neural tissue, readily and accurately implantable as one single unit, without impeding the natural motion of the tissue or causing damage, is critical.

Historically, testing of neuroprosthetic array interfacing has been tested using actual samples of neural tissue. However, some known surrogate tissue models have been developed using different types of silicone elastomer in an attempt to mimic the mechanical properties of real neural tissue, such as spinal cord. One model comprises a SYLGARD® 527 silicone material that is capable of mimicking the ex vivo mechanical properties of human spinal cord in tension. Another model comprises QM Skin 30 silicone elastomer that is capable of simulating the mechanical properties of a human spinal cord in both tension and compression. Neither surrogate tissue, however, is capable of undergoing the extensive deformations that occur in a real spinal cord during identical loading conditions.

Other known surrogate tissue models comprise a collagen casing with an uncrosslinked gelatin filling. For example, attempts to optimize collagen models of spinal cord tissue were made by exposing both the surrogate cord material and in vivo feline cords to the impact of a falling mass and then matching the deformation behavior by adjusting relative concentrations of gelatin to water.

Gelatin filled-type spinal cord models, however, are designed to match the mechanical properties of a real cord in tension and/or compression such that the cord can be embedded with transducers to investigate the mechanisms underlying tissue injury. They are not suitable for use with interfacing microelectrode arrays or for evaluating the mechanical interactions between delicate ISMS microwires or implantable neurostimulators and the spinal cord. More specifically, currently known spinal cord models fail to address the importance of understanding the surface properties of the surrogate material, and the friction that occurs between the array and the cord. These properties can be important in determining how an electrode array may respond when the cord is deformed.

It is understood that relative and non-synergistic movement between an electrode array and its corresponding target tissue during long-term implantation of the array could induce stress and cause potential damage to the tissue. It is desirable to develop an electrode array having improved mechanical biocompatibility (e.g. minimal influence or impact on the tissue itself), and capable of long-term implantation directly into the target neural tissue. The use of such an array would reduce the inaccurate and inefficient implantation of individual electrodes into the tissue, a process which is known to be long, tedious, and impractical.

Thus, there is a need for a physical model of neural tissue that can be used to accurately and effectively evaluate the implantability of electrode arrays. Such a surrogate model may comprise materials having suitable mechanical and surface properties, including surface and interfacial properties that closely match real neural tissue. Such a surrogate model may be used to evaluate the mechanical interactions between neuronal interfacing devices (e.g. flexible-base electrode arrays) and neural tissue, such as the spinal cord.

SUMMARY

A surrogate neural tissue, such as spinal cord, is provided. The method of making the tissue and use thereof, is further provided.

In one embodiment, the present surrogate neural tissue comprises material suitable to mimic spinal cord, and is capable of receiving implanted microelectrodes and microelectrode arrays.

The present surrogate neural tissue may comprise a polymeric elastomer. Preferably, the present surrogate neural tissue may comprise a gelatin elastomer.

The present surrogate neural tissue may be chemically crosslinked. Preferably, the present surrogate neural tissue may be chemically crosslinked with formaldehyde. In one embodiment, the present surrogate neural tissue may comprise formaldehyde crosslinked 9-15 wt % gelatin. Preferably, the present surrogate neural tissue comprises surrogate spinal cord tissue and may, for example, comprise formaldehyde crosslinked 12 wt % gelatin in water.

A flexible-base electrode array having improved biocompatibility and mechanical compliance in the interfacial zone between the array and target neural tissue, such as brain or spinal cord, is provided. The present flexible-base electrode array may have an elasticity or "flexibility" less than or equal to the target neural tissue (e.g. allowing the base and the protruding electrodes to move as a unit and to "move with" the target tissue during deformation). The movement of the electrodes may not be constrained by the present flexible-base electrode array. The present flexible-base electrode array may be capable of receiving at least one electrode and may be customizable for implantation into various neural tissue. The present flexible-base electrode array may be implantable as a single unit.

A method of making the present flexible-base electrode array is further provided.

The use of the present flexible-base electrode array is further provided. The use of the improved array for stimulating or recording neural activity (e.g. instraspinal microstimulation), is further provided.

A flexible-base electrode array adaptable to differing mechanical and surface properties of target neural tissues (e.g. tissue size, shape, flexibility/elasticity/stiffness and curvature) is provided. The present flexible-base electrode array may be implanted into the target tissue as a single unit, while minimizing damage to the tissue during tissue movement.

BRIEF DESCRIPTION OF THE DRAWINGS

FIG. 12 shows the rotation (per mm) of the present flexible-base electrode array when implanted in candidate surrogate cord material;

DETAILED DESCRIPTION OF EMBODIMENTS

Figure 1:
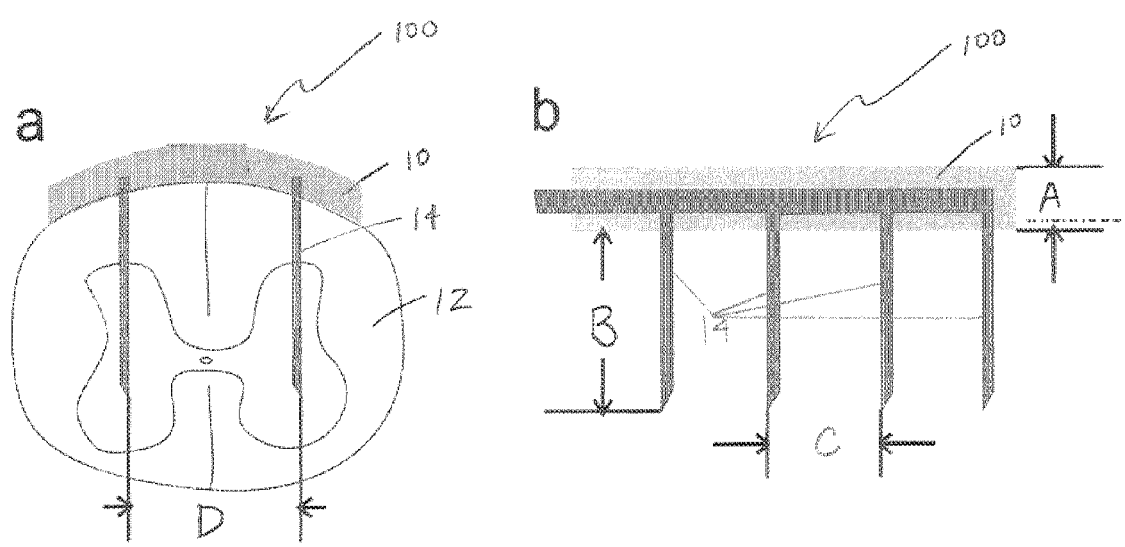
FIG. 1(a) shows a cross-sectional schematic of an example target tissue (e.g. spinal cord) having a flexible-base electrode array implanted into target neural tissue.
FIG. 1(b) shows a longitudinal cross-sectional view of the target tissues and example array.

A flexible-base electrode array for implantation into neural tissue, (FIG. 1), the method of making same and use thereof, are provided. A surrogate neural tissue having mechanical and surface properties similar to neural tissue and capable of receiving an array of microelectrodes for stimulating or recording neural activity, the methods of making same and the use thereof, are also provided. The use of the flexible-base electrode array for stimulating or recording neural activity (e.g. instraspinal microstimulation) and the use of the surrogate spinal cord for receiving and testing electrode arrays for neural interfacing are also provided. The present flexible-base electrode array and surrogate neural tissue are described having regard to FIGS. 1-16.

It should be understood that although reference is made herein to specific types of surrogate tissue, the present surrogate neural tissue may be any neural tissue such as the brain and/or spinal cord. Reference to specific surrogate tissue or its use in combination with the present flexible-base electrode array should not, in any way, limit the scope of the embodiments described herein.

Surrogate Neural Tissue

During daily motion, the spinal cord is subjected to a range of motion, including torsion, flexion and elongation. The extent to which the spinal cord deforms has been determined using motion-tracking experiments and is known to have a maximal strength between 6.8% and 13.6%, on the posterior surface, and between 3.7% and 8.7% on the anterior side. The maximal strain during natural deformation of the cervical spinal cord during neck flexion and extension is 12%. It is desirable to develop a model of spinal cord tissue that can be deformable and elongated to at least 12% of its initial length, or the maximum strain to which a real spinal cord is subjected during daily activities. Such a surrogate cord may be used for in vitro testing of different electrode arrays used in intraspinal microstimulation (ISMS) or other spinal implants such as shunt catheters.

It is desirable to develop a model of spinal cord tissue, or "surrogate" spinal cord, having material characteristics matching as closely as possible the mechanical properties (e.g. deformation behaviour, tensile modulus of elasticity) of real or normal human spinal cord, which may or may not comprise intact pia and dura mater. It is further desirable to develop a model of spinal cord tissue having material characteristics that closely mimic the surface properties of real spinal cord tissue, and is thereby capable of providing near-realistic interactions between the surrogate cord and electrode array implants. Surface properties can be important to understand and characterize for implantation purposes because they can influence electrode design parameters (e.g. insertion behaviour, the force required to penetrate the tissue, the impact of frictional stress caused by electrodes), particularly where the cord undergoes deformation.

It is desirable to develop a model of spinal cord tissue that is capable of receiving implanted microelectrodes, without substantially impeding the mechanical behaviour of the cord, whether individual electrodes or electrode arrays. For instance, it is desirable to provide a surrogate spinal cord that is capable of receiving microelectrodes in a manner that the electrodes move synergistically with the cord and cause minimal damage to the cord. It is further desirable to provide a surrogate spinal cord that is capable of receiving an array of microelectrodes in a manner that the array may synergistically interface or interact with the cord without impeding the mobility of the cord directly beneath the array. Such a spinal cord may eliminate the need to harvest real animal spinal cords.

A surrogate neural tissue, such as spinal cord, is provided. In one embodiment, the present surrogate neural tissue comprises material suitable to mimic spinal cord, and is capable of receiving implanted microelectrodes. The present surrogate neural tissue may comprise a polymeric elastomer. Preferably, the present surrogate neural tissue may comprise a gelatin elastomer. The present surrogate neural tissue may be chemically crosslinked. Preferably, the present surrogate neural tissue may be chemically crosslinked with formaldehyde. In one embodiment, the present surrogate neural tissue may comprise formaldehyde crosslinked 9-15 wt % gelatin. Preferably, the present surrogate neural tissue comprises surrogate spinal cord tissue and may, for example, comprise formaldehyde crosslinked 12 wt % gelatin in water.

The present surrogate spinal cord will now be described by way of the following example.

Example

Surrogate Spinal Cord

The present surrogate spinal cord material was developed using a number of methods on a variety of materials. For instance, a variety of silicone elastomers and gelatin formulations were examined. By way of information, gelatin is a hydrogel material derived from collagen and is highly tunable through variations in hydration and crosslinking. It is known to use gelatin/hydrogel to fabricate surrogate spinal cord, however, the quality and characteristics of such surrogate spinal cord's surface properties is unknown and a crosslinker has not been used (which would prevent the cord from falling apart during handling). In contrast, known models of gelatin surrogate spinal cords utilize a casing, rather than a crosslinker.

Each candidate material was evaluated to determine the tensile modulus, using dynamic mechanical analysis (DMA), indentation testing and frictional forces to characterize the surface properties of the materials (e.g. the amount of force required to withdraw a needle at a controlled speed from a surrogate cord).

The cord/electrode interactions of each candidate cord was then evaluated when the cord was deformed in tension using arrays of individual microwires without a base, and an array of 8 microwires connected to a base. These arrays were embedded in the surrogate cords onto which surface markers were drawn, and the geometry of the cords were observed optically before and during a 12% extension to assess the movement of the electrodes within the cord. Interfacial properties, which control the stress that develops between the cord and the implanted object, were also observed by measuring the force required to pull a stainless steel needle out of the surrogate cords at a controlled rate. Interfacial interactions can be used to determine the mechanical stability of intraspinal implants. Where such factors are not considered, problems can arise where inappropriate interfacial properties result in very high friction between the surrogate material and the implant, and ultimately the destruction of the implant. In addition, these constructs may be used to test the mechanical stability of brain implants, since the mechanical and interfacial properties of tissue in the brain are similar to spinal cord tissue.

Candidate Materials and Methods of Manufacture

Silicone Elastomers: SYLGARD® 184 was obtained from Dow Corning Ltd. (Midland, Mich., USA) as a two component system (elastomer and crosslinker), and was prepared by mixing the two components in ratios of elastomer:crosslinker of 10:1, 20:1, 30:1, 40:1 by weight. Samples were crosslinked by baking at 60° C. for 3 hours. QM Skin 30 was obtained from Quantum Silicones LLC (Richmond, Va., USA), and was prepared by mixing the two components in ratios of 10:1 (as directed) and cured for 24 hours at room temperature. TCB 5101 was obtained from BJB Enterprises, Inc. (Tustin, Calif., USA), and samples were prepared by mixing the two components in a 1:1 ratio (as directed) and cured in an appropriate mold for 24 hours at room temperature.

Gelatin Elastomers: Gelatin powder (G1890, gelatin from porcine skin, Sigma Aldrich, Oakville, Ontario, Canada) was used to prepare a solution of water and gelatin having 10%-20% gelatin by weight, or any amount therebetween. In one embodiment, gelatin elastomers having 10%-20% gelatin by weight, and preferably 12%-15%, or any amount therebetween, was prepared. For example, to prepare uncrosslinked 9 wt %, 12 wt % and 15 wt % gelatin in water, a suitable mass of powder was dissolved in distilled water. To prepare the 12 wt % gelatin in water, 2.73 g of powder was dissolved in 20.0 g of distilled water. Solutions were heated to a temperature between 40° C.-60° C., and preferably to 53° C.-58° C., or any temperature therebetween, and stirred at a rate of 60 revolutions per min until the gelatin was dissolved (approximately 20 minutes). Where applicable (and to enhance stability of the surrogate cord material), a suitable crosslinking agent, such as formaldehyde (143 mL, 19.4 mmol/100 ml) was added to the solution, and the solution was allowed to cool to a temperature between 40° C.-50° C., and preferably between 42° C.-47° C., and stirred until the crosslinking agent was dissolved (approximately 15 minutes). Optionally, gold nanoparticles (G1527 Gold colloid solution, Sigma Aldrich, Oakville, Ontario, Canada; or other suitable CT contrasting agents) may be added to the chemically crosslinked gelatin solution as a micro-CT contrasting agent. For example, 1.0 mL gold nanoparticles may be added after the crosslinking reaction and stirred (approximately 3 minutes at 45° C.). Measurements were made to ensure the gold nanoparticles did not alter the mechanical properties of surrogate cord material. The solutions were then poured into a mold having a predetermined size and shape, as dictated by the particular neural tissue being modelled, and allowed to set or cure. The surrogate tissue was then removed from the mold.

Surrogate cords with elliptical cross-sections (6 mm×8 mm) were prepared by curing candidate materials in a custom-made aluminum mold. The dimensions of the elliptical cross-section of the mold were based on magnetic resonance images (MRIs) of lumbosacral regions of cat spinal cord. It is understood that the cat is the primary model for intraspinal microstimulation implants rendering the presently determined mechanical interactions of implants and the surrogate cords comparable to other histological and electrophysiological results. Moreover, the closeness of the cross-sectional dimensions of the spinal cord in cats and humans may allow for the experimental results to be readily translated to humans. In one embodiment, the length of each as-molded cord was 7 cm, but it is understood that the cords could be cut to any desired length. Samples were typically cured overnight in the mold (wrapped in plastic to minimize drying), and characterized the following day. When preparing silicone cords, the mold was pre-coated with vacuum grease (Dow Corning, High Vacuum Grease, Midland, Mich.) to prevent the silicones from bonding to the surface of the mold. Rat spinal cords were harvested and utilized for comparative purposes in indentation and frictional force testing.

Tensile Modulus

Figure 2:
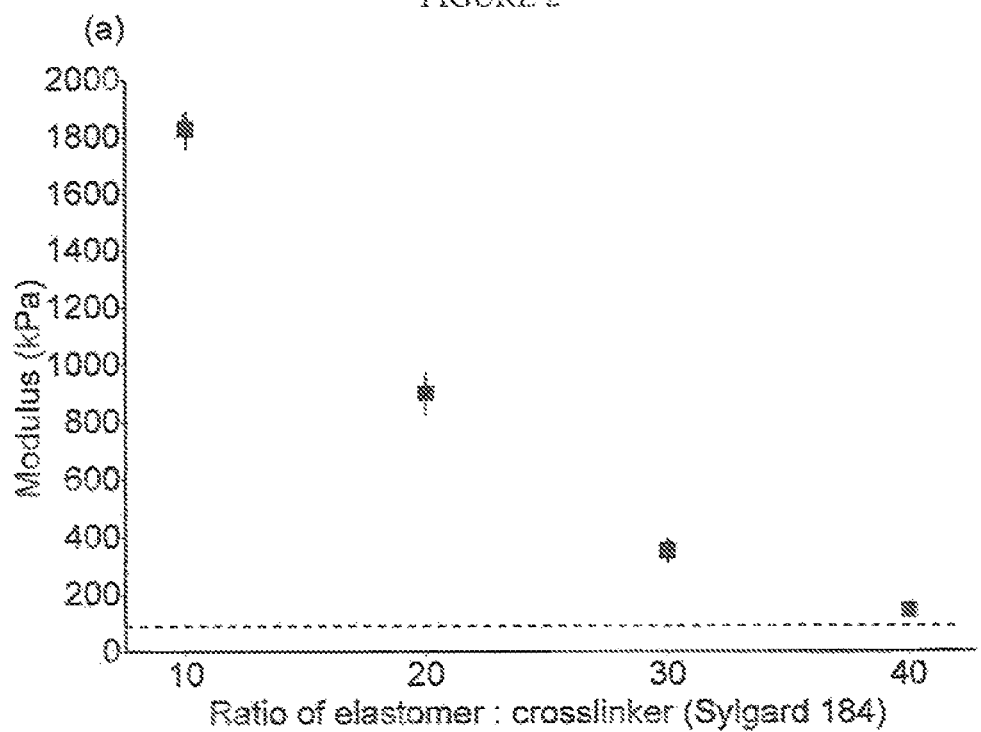
FIG. 2(a) depicts the tensile moduli of elasticity of example candidate surrogate spinal cord material SYLGARD® 184.
FIG. 2(b) depicts the tensile moduli elasticity of candidate spinal cord materials SYLGARD® 184 (square), TCB 5101 (circle) and QM Skin 30 (triangle)
Figure 2:
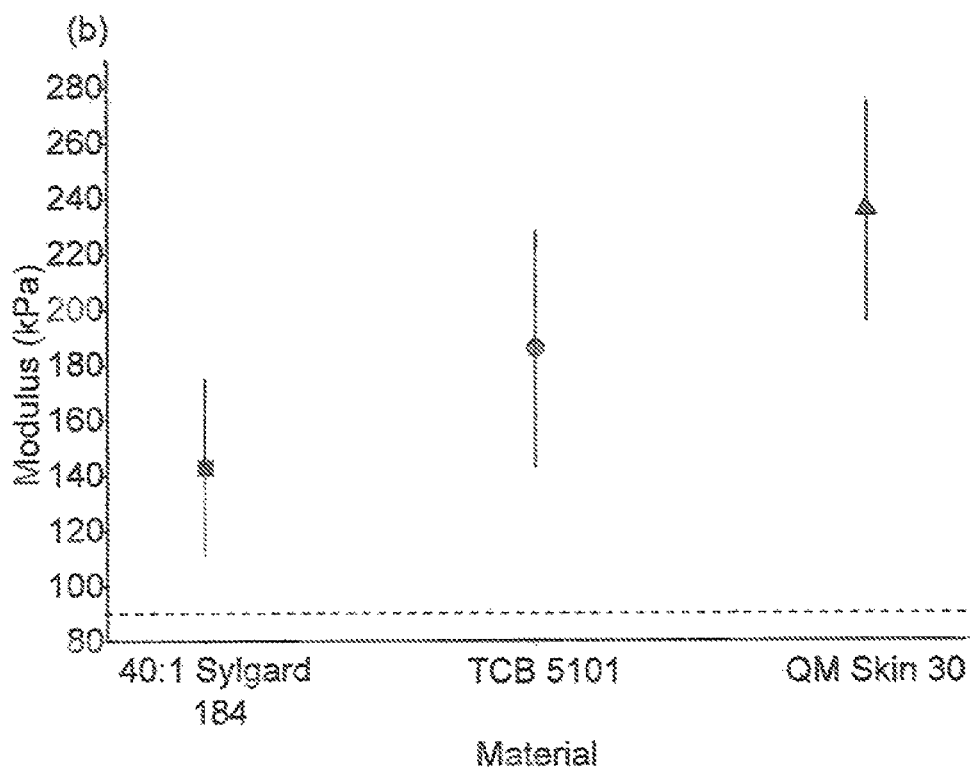

Having regard to FIG. 2, the uniaxial tensile modulus of the candidate materials was measured using Dynamic Mechanical Analysis (DMA, Perkin Elmer DMA 8000, Waltham, Mass., USA). Flat, hydrated gelatin samples having a rectangular cross-section were cut into dimensions of approximately 11 mm×7.5 mm×3.5 mm (length×width×thickness), and silicone samples having a rectangular cross-section were cut to have dimensions of approximately 13 mm×7 mm×2 mm. Samples were loaded into the DMA apparatus and clamped at a typical sample length of ~6 mm. All tests were taken at room temperature (in the range of 21.7° C. to 25.5° C.). During characterization, the displacement and frequency of the strain were controlled to 0.01 mm and 1 Hz respectively, to minimize the viscous component of the response. For each material, a minimum of 3 different samples was measured, and each sample was characterized 3 times.

The modulus of each candidate material was measured using dynamic mechanical analysis in tension mode. FIG. 2($a$) depicts the moduli of elasticity for crosslinker:elastomer ratios of the SYLGARD® 184 silicone elastomer (at mixing ratios (base:crosslinking agent) of 10:1, 20:1, 30:1 and 40:1), while FIG. 2($b$) depicts the results for three different types of silicones tested, namely, SYLGARD®184 mixed in a 40:1 ratio, TCB 5101 and QM Skin 30. Average value and standard deviation are shown, based on a minimum of 3 different samples, each of which were tested 3 times. The modulus of elasticity of all materials was significantly different from the target modulus of 89 kPa ($p<0.05$), shown as the horizontal dashed line.

Figure 3:
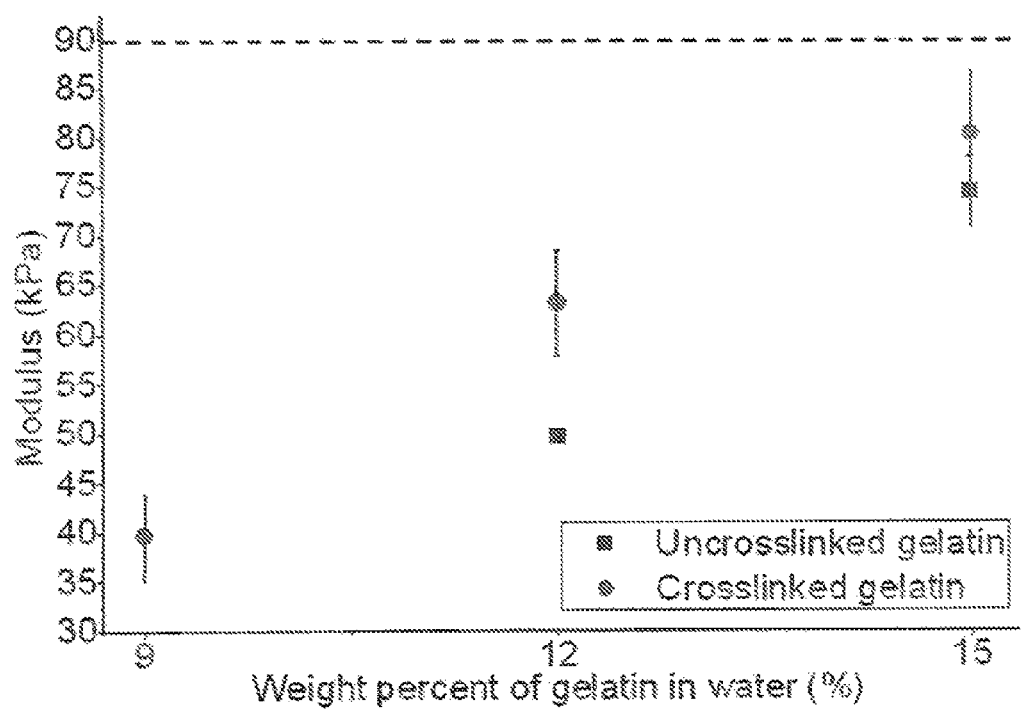
FIG. 3 depicts the tensile moduli of elasticity of example candidate surrogate spinal cord material uncrosslinked (square) and crosslinked (circle) hydrated gelatins.

FIG. 3 depicts the moduli of elasticity of uncrosslinked (square) and formaldehyde crosslinked (circle) gelatin samples composed of various concentrations of gelatin in water (9, 12 and 15% gelatin weight in water). The modulus of the uncrosslinked 9 wt % gelatin was less than the minimal value that could be reliably measured in tension mode by DMA (<40 kPa). The uncrosslinked gelatin samples had lower moduli than the crosslinked gelatin at the same weight percent in water. The crosslinked 15 wt % gelatin was most similar to the target modulus (79.6 kPa±11.7 kPa, t=0.8), while the modulus of the crosslinked 12 wt % gelatin was also close (65 kPa±6 kPa, t=3.7). Only the modulus of the crosslinked 15 wt % gelatin was not statistically different from the target modulus. Because the standard deviation of the target modulus obtained from the literature is unknown, and the surrogate materials were measured under different conditions from the real human spinal cord from which the target modulus was derived, the discrepancy between the crosslinked 12 wt % gelatin and target value may be tolerated when considering its suitability for use in the surrogate cord.

Indentation Testing

Measurements of modulus of elasticity of ex vivo spinal cord samples are not easily achieved using the DMA method described above. As such, indentation testing was performed in order to compare the mechanical properties of surrogate materials and real, ex vivo spinal cords under identical conditions. Measurements were obtained from rat cords with pia mater intact. Surrogate cords were prepared from each candidate material using the aluminum mold with cross-sectional dimensions corresponding to those of the cat lumbosacral spinal cord. It is understood that the difference in the cross-sectional dimensions of cat (6 mm×8 mm) and rat spinal cords (2 mm×3 mm) will not likely affect the outcome of the indentation tests, which are conducted to a maximum depth of 1 mm.

The force required to achieve similar indentations of the surrogate and rat spinal cords, an indenting arm was used to displace a cono-spherical tip with a 1.7 mm diameter into the sample. The vertical position of the indenter was varied using a micrometer, and the force resulting at the tip during this displacement was recorded using a force transducer.

Two cords of each material and two rat spinal cords were tested. The testing was repeated at three different spots for each cord (one at each end, and in the middle). Gelatin cords were sealed in plastic during testing to reduce drying, although a small hole was cut through which the tip could access the cord. Prior to each test, the indenter was lowered until the tip was just in contact with the top surface of the cord, and the force transducer was set to 0 N. For each indentation, the tip was displaced at increments of 0.05 mm for the first 0.5 mm, and then at increments of 0.1 mm until the indenting depth reached 1 mm and the force was recorded.

Figure 4:
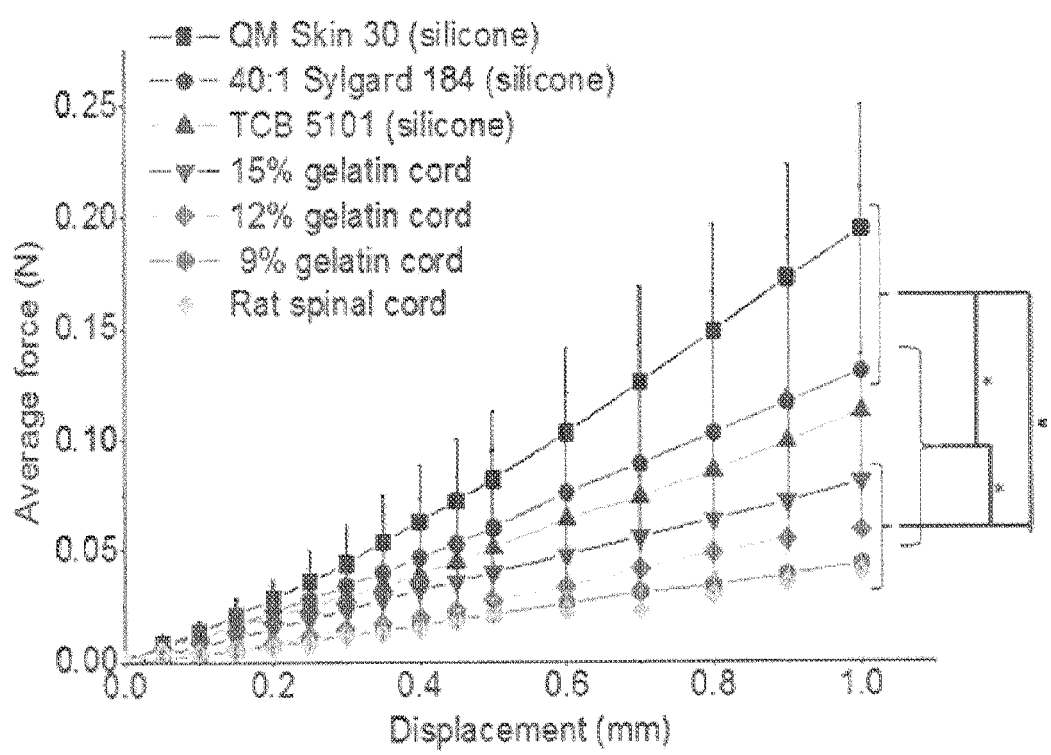
FIG. 4 depicts the force of indentation of silicone and gelatin candidate surrogate spinal cord materials and rat spinal cords.

Having regard to FIG. 4, the average force of indentation required to achieve specific displacements of silicone, gelatin and rat spinal cords are shown, as well as the slope calculated for each sample based on a linear fit (m). Larger indentation forces were required for each silicone elastomer to achieve the same depth as for the rat spinal cords, while the QM Skin 30 required the highest forces of indentation for all the materials tested. For the gelatin cords, the force required to achieve a specified displacement in each type of gelatin surrogate cord was consistently closer to the force required to achieve the same displacement in the rat spinal cords. The slopes of the force-displacement curves of the formaldehyde crosslinked 9 wt % and 12 wt % gelatin in water cords (0.045 and 0.063, respectively) were close to that of the rat spinal cord. At each indentation depth, the force required to indent the formaldehyde crosslinked 9 wt % gelatin cords fell within the standard deviations of the rat spinal cord. The standard deviations of the crosslinked 12 wt % gelatin cord and rat spinal cord overlapped with each other, indicating strong similarities in their indentation behavior. This was despite the differences in moduli measured by DMA. Moreover, the 12 wt % samples were deemed by an experienced spinal cord physiologist to "feel" more similar to both rat and cat spinal cords than the gelatin cords containing 9 wt % or 15 wt % gelatin in water.

Frictional Force Tests of Surrogate and Rat Cords

Figure 5:
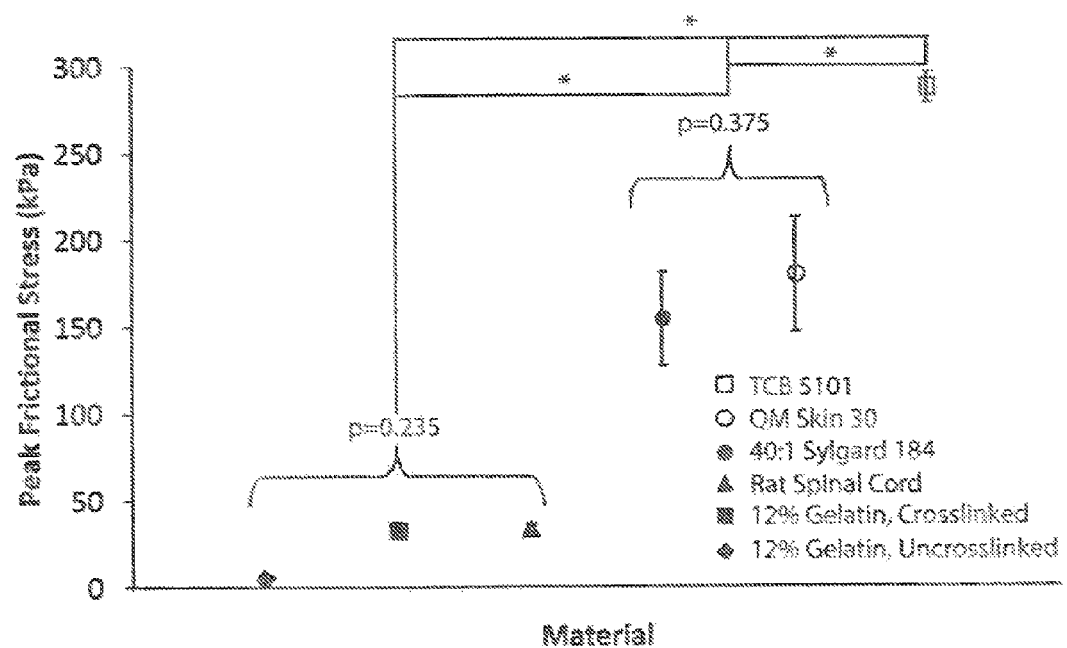
FIG. 5 provides frictional stress measurements for silicone and gelatin candidate surrogate spinal cord materials and rat spinal cords.

Having regard to FIG. 5, frictional forces between the candidate spinal cord materials and a standard stainless steel needle were examined. Friction force testing, to determine the frictional force between a 30 gauge stainless needle and the surface of candidate cord materials and rat spinal cord, was performed using an Instron 4443 Force Tester (Grove City, Pa., USA). Testing was done by mounting a 1 cc syringe fitted with a 30 gauge needle to the moving head of the Instron tester. Force was measured while the needle pushed downward for 5 mm and pulled upward for 4 mm at a pulling rate of 0.3 mm/min. FIG. 5 depicts the peak frictional stress values. The uncrosslinked 12 wt % gelatin samples had the lowest frictional stress, followed by the formaldehyde-crosslinked 12 wt % gelatin samples.

Figure 6:
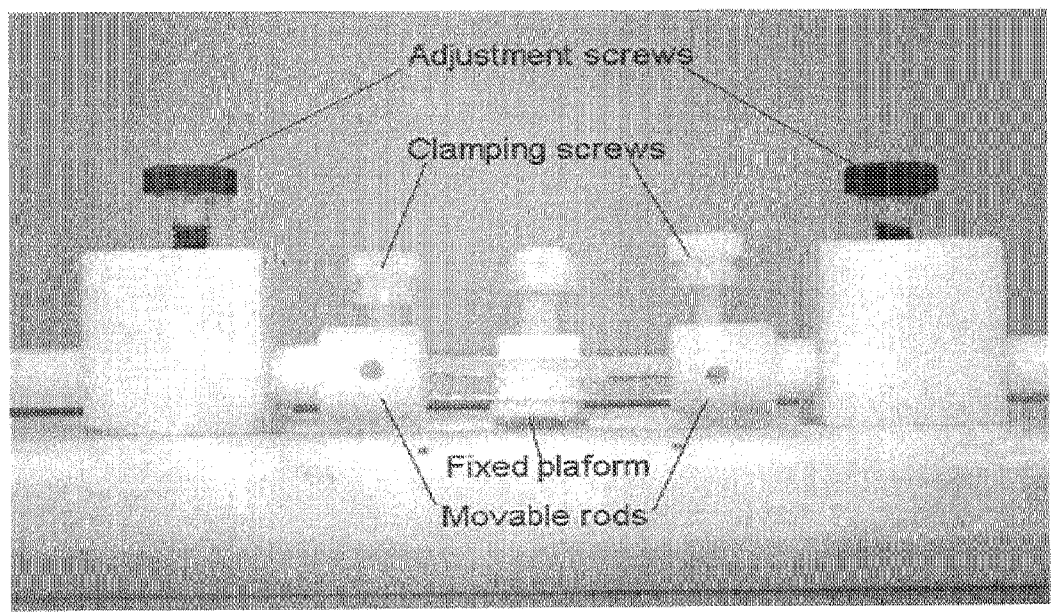
FIG. 6 depicts an exemplary stand capable of receiving and securing neural tissue such as silicone and gelatin candidate surrogate spinal cord materials and rat spinal cords.

Mechanical Interaction Between Implanted Electrode Arrays and Surrogate Spinal Cord To determine whether candidate surrogate cords could receive implanted microelectrode arrays and still undergo typical ranges of motion, candidate materials were positioned in a stand such as, for example, the stand depicted in FIG. 6. The stand comprises a fixed platform, which can be raised or lowered to support the cord material, and two adjustable rods which can be moved laterally to apply tension thereto. Clamping of the cord within the stand was facilitated by coating the ends of the cords with a thick layer of epoxy (MG Chemicals Fast Set Epoxy 8332, Surrey, British Columbia, Canada), which was allowed to set overnight at 4° C. The cords were then soaked in water at 4° C. for 24 hours before experimentation to ensure that they were thoroughly hydrated and to minimize the drying before the measurements.

Figure 7A:
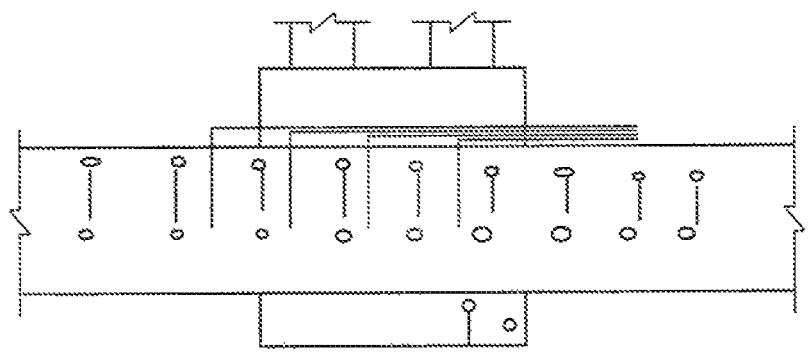
FIG. 7 depicts candidate surrogate cord material implanted with: individual microwires, 7(a); electrodes held together by a rigid base, 7(b); or no implant, 7(c).
FIG. 7(d) provides a schematic diagram of the candidate surrogate spinal cord/implant interaction.
Figure 7B:
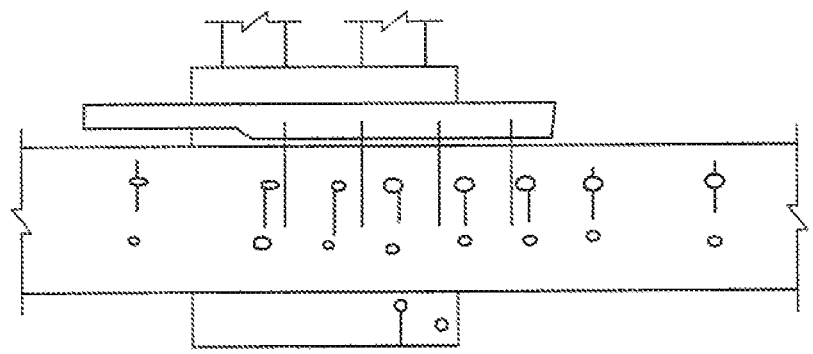
Figure 7C:
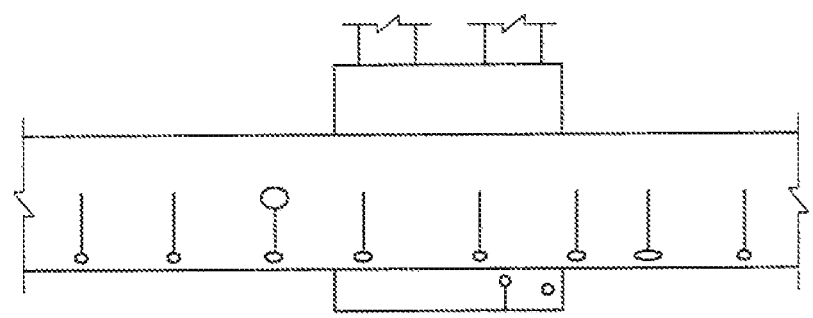
Figure 7D:
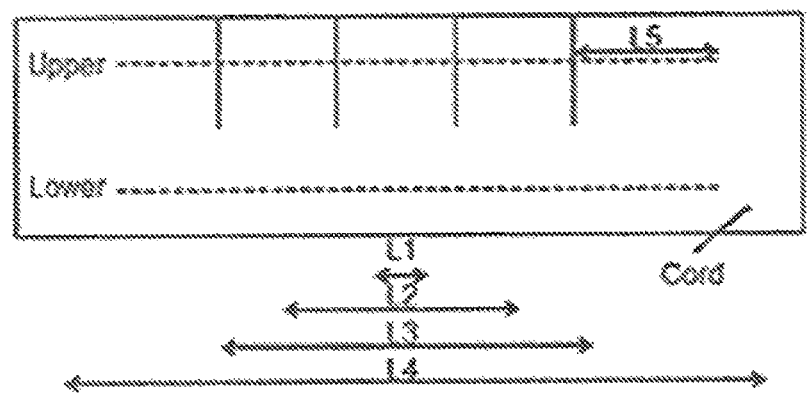
Figure 8A:
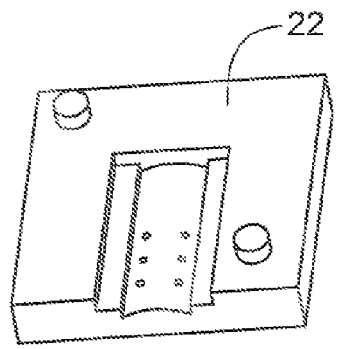
FIG. 8 depicts exemplary molds used to fabricate the present electrode array, the mold having a female portion (a-b) and a male portion (c-d)
Figure 8B:
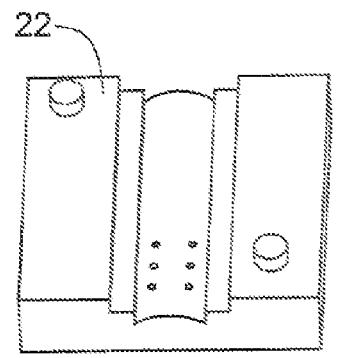
Figure 8C:
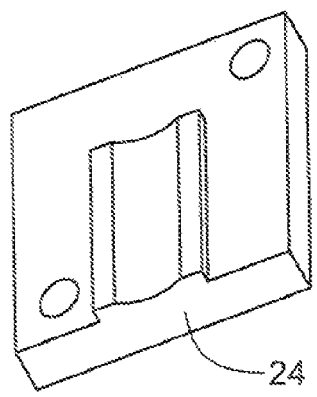
Figure 8D:
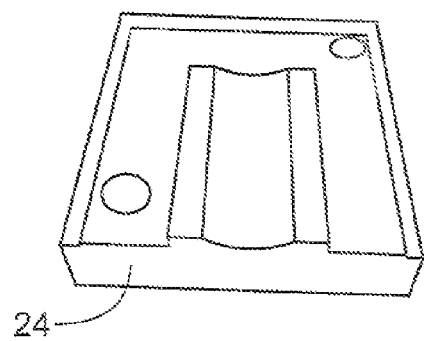

As depicted in FIG. 7, two types of electrode arrays were examined: one consisting of independently positioned 30 μm wires (FIG. 7(a)) and one consisting of 75 μm wires positioned at pre-determined locations in a rigid base (FIG. 7(b)). It is understood that the latter array may be representative of arrays typically used in the art for stimulating or recording from structures in the central nervous system. Both arrays contained 2 rows of 4 microwires (FIG. 7(d)). As a reference, the same tests were also performed on a surrogate cord that had not been implanted with any electrodes (FIG. 7(c)).

By way of example, formaldehyde crosslinked 12% gelatin surrogate cord material was positioned on the stand, secured in place using the clamping screws, and was elongated by 12% of its initial length using the adjustment screws. To visualize the distribution of strain within the cord under elongation, four pairs of reference dots were drawn on the surface of the cord in India ink. At least three pictures of each configuration were taken using a Canon EOS 1000D camera (Rockville, Md., USA) as the cords were relaxed and stretched. The distance between the reference markings was measured before and after the deformation was applied from the pictures using both Adobe Illustrator and AxioVision software, and the results were used to determine the resulting strain in different parts of the cord. To calculate the distance between markings in absolute units (mm), the dimensions of the stand itself were used to calibrate the measurements.

Unimplanted cord material showed uniform deformation throughout the cord. Cord material implanted with arrays having individual microwires deformed in a manner similar to deformation information for prior art material, ranging from 9±1% to 13±1%, while cord material implanted with rigid-base arrays was smaller, ranging from 3±1% to 7±1%, suggesting that the rigid-base array inhibited deformation of the cord. Further, deformation between the upper markers was smaller than that between the lower set of markers, which may be because the deformation of the cord was impeded by the base.

Flexible-Base Electrode Array

It is desirable to develop an electrode array that can readily be modified, and that is adaptable to the mechanical and surface properties of any target neural tissues (e.g. tissue size, shape, elasticity and curvature), which vary highly between tissue type and location. It is contemplated that the target neural tissue may comprise any neural tissue such as, for example, the brain, the spine or nerves, and may be characterized by MRI (see FIG. 16). As such, the present flexible-base electrode array may be adaptable to correspond to tissue properties that vary between subjects, as well as within the subject's own tissue (e.g. different neuron activation pools in the spine can have different locations in the ventral horn of the cord).

The present flexible-base electrode array may be capable of receiving electrodes, wherein the receipt of the electrodes minimally influences the biocompatibility of the array. More specifically, the present characteristics of the present array (size, flexibility/stiffness, curvature, and electrode size/length/density) may be modifiable and adaptable to match the mechanical and surface properties of the target tissue with which it will interface, thereby reducing damage or stress caused by the array on the neural tissue.

A flexible-base electrode array (FIG. 1) having improved biocompatibility and mechanical compliance in the interfacial zone between the array and target neural tissue, such as brain or spinal cord, and methods of making same is provided. The use of the improved array for implantation into target tissue, and for stimulating or recording neural activity (e.g. instraspinal microstimulation), is further provided.

The present flexible-base electrode array will now be described by way of the following example.

Example

Flexible-Base Electrode Array

Flexible-Base Electrode Array Apparatus and Method of Manufacture

The biomechanical compatibility of the present electrode array was examined by implanting the array into the present surrogate neural tissue. More specifically, viability of the present electrode array was examined by implanting the array into the present surrogate spinal cord and subjecting the tissue to deformations representative of those experienced by real spinal cord tissue. It is understood that injury and damage to the surrogate tissue could be examined by any known methods such as, for example, by micro-CT scan alone, or by micro CT scan in the presence of gold nanoparticles.

Having regard to FIG. 1, the present electrode array 100 may comprise a base 10, and preferably a flexible base. The base 10 may comprise predetermined characteristics such as, for example, size, shape, thickness "A", flexibility/stiffness and curvature as may be commanded by the size, shape, thickness, flexibility/stiffness and curvature of the corresponding target tissue 12 with which it interfaces. For example, the thickness of the base 10 may be uniform along its longitudinal axis, and the base 10 may also form a curved cross-section to reflect the surface geometry of the target tissue, i.e. the spinal cord. It is contemplated that employing an array 100 having a configuration matching the corresponding to the target tissue may reduce the extent of connective tissue formation between the base 10 and the tissue with which it interfaces 12, thereby minimizing dislodgement of the array 100.

The base 10 may be fabricated using a precursor (e.g. curable in a mold) base material. The base material may comprise suitable known biocompatible polymers. The base 10 may be fabricated of polydimethylsiloxane (PDMS). In one embodiment, the base 10 may comprise a commercially available biocompatible silicone elastomer, such as, for example, MED 6215 (NuSil Technology, Carpinterial, Calif., USA). The MED 6215 silicone elastomer may be used as received and may be prepared in the suggested elastomer to crosslinker ratio, with a mixing ratio of 10:1. It is understood that any suitable material having a moduli of elasticity approximately orders of magnitude smaller than that of other polymers, such as polyimide and parylene, may be used. It is contemplated that the base 10 may be fabricated to be more or as flexible as the target tissue (e.g. equal or less stiff or "rigid" than the target material).

The base 10 may further comprise at least one electrode 14 protruding therefrom. The at least one electrode 14 may depend downwardly and substantially perpendicularly from the base 10. In one embodiment, the base 10 may comprise at least one row of at least one electrode 14 (see FIG. 1(b)). Preferably, the base 10 comprises two rows of at least one electrode 14 protruding therefrom. The at least one electrode 14 may comprise stainless steel microwires such as, for example, 30 μm or 80 μm SS wires (California Fine Wire, Grover Beach, Calif., USA), or any other size as may be suitable. Where the present array 100 comprises more than one at least one electrode 14, the at least one electrodes 14 may be spaced apart at predetermined intervals "C" along the base 10. For instance, the at least one electrodes 14 may be provided in pairs and may be spaced at approximately 3 mm intervals along the length of the base 10. Where the present array 100 comprises more than one row of at least one electrode 14, the rows may be spaced apart at a predetermined distance "D" along the base 10.

It is understood that the at least one electrodes 14 may be fabricated in any material and in any size and shape that is suitable for the particular target tissue 12. For example, it is contemplated that either platinum/iridium (Pt/Ir) or stainless steel (SS) microwires (30 μm in diameter), as well as multi-contact microfabricated cylindrical electrodes (85 μm in diameter) may be used. The at least one electrode 14 may be positioned as necessary (e.g. bent) to achieve a desired height to form a continuous electrode-lead. For example, where target height "B" for the at least one electrode 14 will vary depending upon the electrode used and the tissue being targeted. In the present Example, the target height of the at least one electrode may range between approximately 1.95-2.03 mm. Where the at least one electrodes 14 are provided in more than one row, the inter-row and inter-electrode spacing of electrodes may vary depending upon the size of the at least one electrode 14 and the tissue being targeted. In the present Example, the inter-row and inter-electrode spacing may be approximately 4±0.09 mm and the inter-electrode spacing may be approximately 3.0±0.09 mm.

The base 10 may be fabricated in a mold 20 designed with, for example, 3D CAD software (Pro/Engineer Wildfire 3.0, Parametric Technology Corporation, Needham, Mass., USA; FIG. 8). Once designed, the mold 20 may be manufactured using a rapid prototyping (3D printing), and glossy smooth surfaces may be obtained using Objet FullCure720 (Objet Ltd, Billerica, Mass., USA). A glossy surface may be used to minimize any potential bond between the surface of the mold 20 and the base 10 formed therein. The molds 20 may cleaned then placed in sodium hydroxide solution, prepared by mixing 10 g of NaOH (Anachemia Canada Inc., Quebec, Canada) in 500 ml of distilled water, for 1 hour and cleaned again.

More specifically, the mold 20 may comprise a female portion 22 (FIGS. 8(*a*)-(*b*)) that may be modified to accommodate and configure the characteristics of the base 10 formed therein (including curvature). The female portion 22 may be capable of receiving at least one electrode 14 to be secured within the base 10. For example, the shape and curvature of the base 10 formed in the mold 20 may be modified by adjusting the shape and curvature of the female portion 22 of the mold 20.

Positioning holes may be formed in the female portion 22 (see FIG. 8*b*), through which the at least one electrode 14 may be inserted, thereby determining the location and density of the at least one electrode 14 in the base 10. The positioning holes may formed by feeding small (X um) wires (corresponding to the size and shape of the at least one electrode 14) through the mold prior to curing. The location of the positioning holes may correspond to a desired location of the target tissue 12. For example, the positioning holes may be located such that the arrangement of the at least one electrode 14 within the array 100 will approximately correspond to the regions of motor neuron pools within target tissue (as may be determined by MRI), thereby allowing for activation of different target muscles and movement synergies.

The mold 20 may further comprise a male portion 24 (FIGS. 8(*c*)-(*d*)), for corresponding to the female portion 22, and capable of controlling the width or thickness of the base 10. The male portion 24 may be used to shape a near uniform thickness along the length of the base 10. The male portion 24 may also be used to shape the thickness of the base 10 to be substantially greater than the length of the at least one electrode 14 (see FIG. 1(*b*)). The mold 20 may be open at both ends to facilitate heat transfer and solvent evaporation.

Once the mold 20 is prepared, the at least one electrode 14 may be inserted through the positioning holes, and the precursor material for the base 10 may be introduced to the mold 20.

The at least one electrode 14 may be inserted through the positioning holes and into the precursor base material, and the precursor base material may be allowed to cure. Height and spacing of the at least one electrode 14 may be controlled, as the height of the at least one electrode 14 can affect the accuracy of the electrode tip placement in the target tissue 12, and the spacing or density of the at least one electrodes 14 can impact the overall flexibility of the array 100. Once the at least one electrode 14 is positioned, the samples may be left to set for approximately 60-90 minutes at a temperature of approximately 66° C. After curing, the base 10 may be removed from the mold 20.

It is contemplated that the base 10 may have a reduced thickness, thereby improving the implantability of the array 100 within the target tissue 12 (where space may be limited), while maintaining sufficient stability to support the at least one electrode 14. Preferably, the base 10 may be approximately 30 μm in diameter. It is understood that any thickness of the base 10 that may resist tearing during deformation of the tissue 12 is suitable. For example, a base 10 thickness of approximately 10 times thicker than that of the diameter of the at least one electrode 14 may be appropriate. It is understood that bases 10 having differing thicknesses may be designed for use with different target tissues 12 (e.g. for use in felines, a base having a thickness of ~300 μm may be desired). Where the base 10 is desired to have a thickness of approximately 1 mm, the mold 20 may be fabricated by being silanized in a vacuum chamber dessicator, with a drop of trichloro(1,1,2,2-perfluorooctyl)silane, in order to prevent the base 10 (which may comprise polymerized silicone elastomer) from sticking to the surface of the mold 20 when removed therefrom. It was noted that 300 μm bases 10 were not able to fully polymerize in 300 μm thick molds 20 due to surface inhibition effects that became dominant as the thickness of the mold 20 was reduced. Therefore, in some embodiments, it may be necessary to utilize a thicker mold 20 (e.g. 398 um), lined on each side with a thin (e.g. 49 um) layer of polypropylene.

Figure 9:
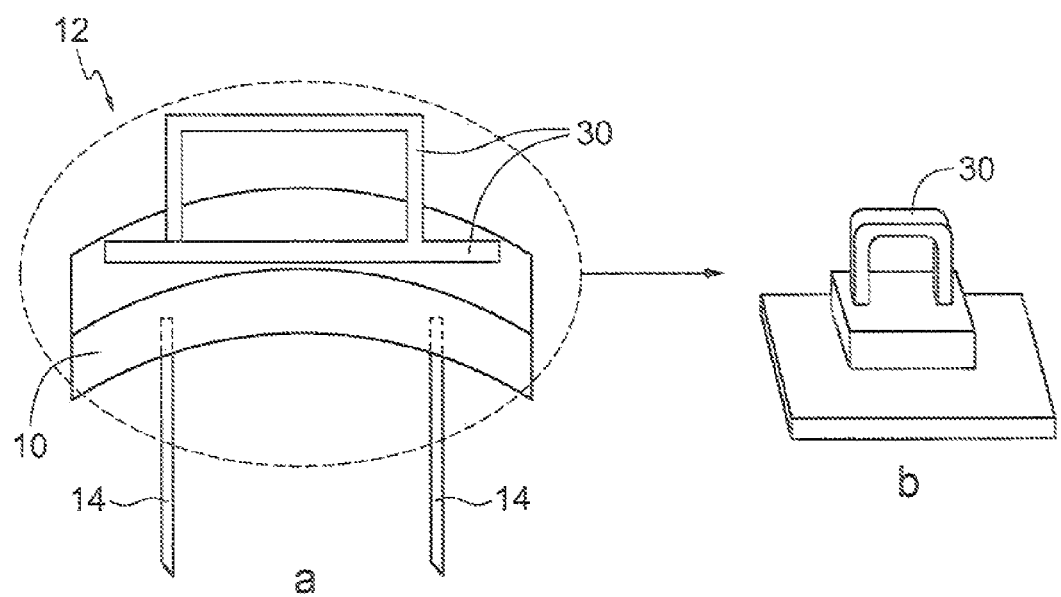
FIG. 9(a) shows a cross-sectional schematic diagram of a temporary flexible handle adhered to the base of the present flexible-base electrode array.
FIG. 9(b) is a perspective view of the flexible handle adhered to the base.

In order to facilitate handling of the array 100, and to preserve the structural integrity of the implantation, a temporary handle 30 may optionally be positioning on the top of the base 10 (see FIG. 9). Handles 30 may be designed in 3D CAD software and rapid prototyped. Handles 30 may be adhered to the base 10 using, for example, a photopolymerizable glue prepared by mixing polyethylene glycol diacrylate (PEGDA, molecular weight 575, Sigma-Aldrich) with 0.5 wt % photoinitiator (Irgacure 651, CIBA). The top surface of the base 10 may initially be treated by UV ozone (for ~10 minutes) to improve adhesion of the handle 30. The adhesion compound may be applied to the handle 30 and the handle positioned on the surface of the base 10. Both base 10 and handle 30 may then be polymerized for 10 minutes by exposing the base 10 and the handle 30 to UV light (e.g. under an 8 W UV lamp at 365 nm approximately 5 cm away).

Tensile Testing

The elastic modulus of the base 10 was characterized using an Instron single column tabletop system with 1 kN load cell (Model 5943, Instron, Norwood, Mass.), according to known ASTM standard D412D. The modulus of MED 6215 used to prepare the exemplary base 10 described herein was determined to be 1.0 MPa, and this value was utilized in the finite element model.

Elongation Testing

Figure 10:
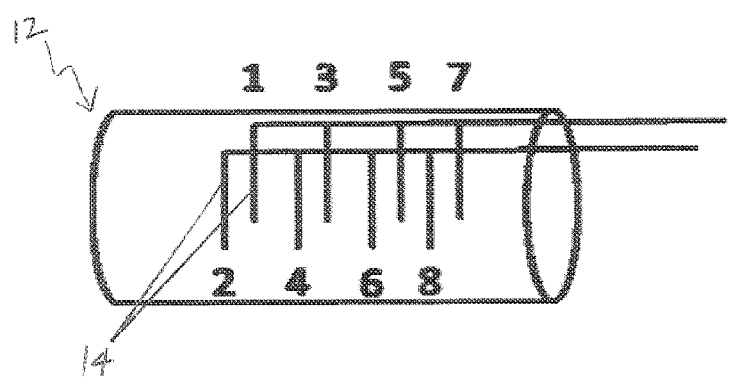
FIG. 10(a) depicts a schematic of the flexible-base electrode array according to embodiments herein showing two rows of electrodes implanted in candidate surrogate cord material.
FIG. 10(b) depicts example markings used for measuring electrode placement.
Figure 10:
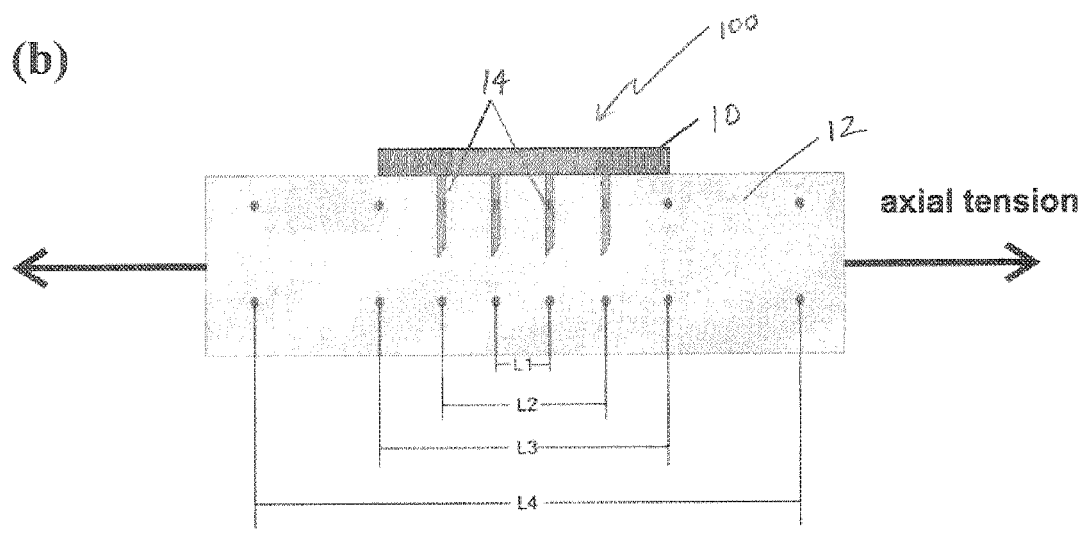

Having regard to FIG. 10, one embodiment of the present flexible-base electrode array 100 (having two rows of the at least one electrode 14) was implanted into the target tissue 12. The particular array 100 tested comprised 2 rows of 4 electrodes 14 with a diameter of 30 μm, base thicknesses of both 1 mm and 300 μm embedded with straight lead wires (30 μm in diameter). The inter-row separation was 4 mm, and the inter-electrode spacing was 3 mm. It is understood that any configuration of electrode height and spacing may be provided. The array 100 was implanted into the target tissue 12 prepared as described herein, and mounted onto the stand (FIG. 6), and subjected to axial tension (FIG. 10(*b*)). In this Example, the target tissue 12 was subjected to approximately 12% axial strain, however it is understood that any strain relevant to mimic real neural tissue may be employed. Two rows of reference dots (L1-L4) placed on the upper and lower surfaces of the target tissue 12 were used to measure the strain imposed upon the tissue 12 and to evaluate the interaction between the array 100 and the tissue 12.

In this Example, the biomechanical properties of the present flexible-base electrode array 100 was assessed by comparing the reaction of the target tissue 12 to other target tissue 12 samples placed under similar strain and having either no implant (control), implants of individual electrodes (no base), or implants of electrode arrays in which the electrodes were held together by a rigid base (e.g. the known rigid-base McCreery array having two rows of 75 μm electrodes embedded in pairs at 3 mm intervals along the length of the base).

Figure 11:
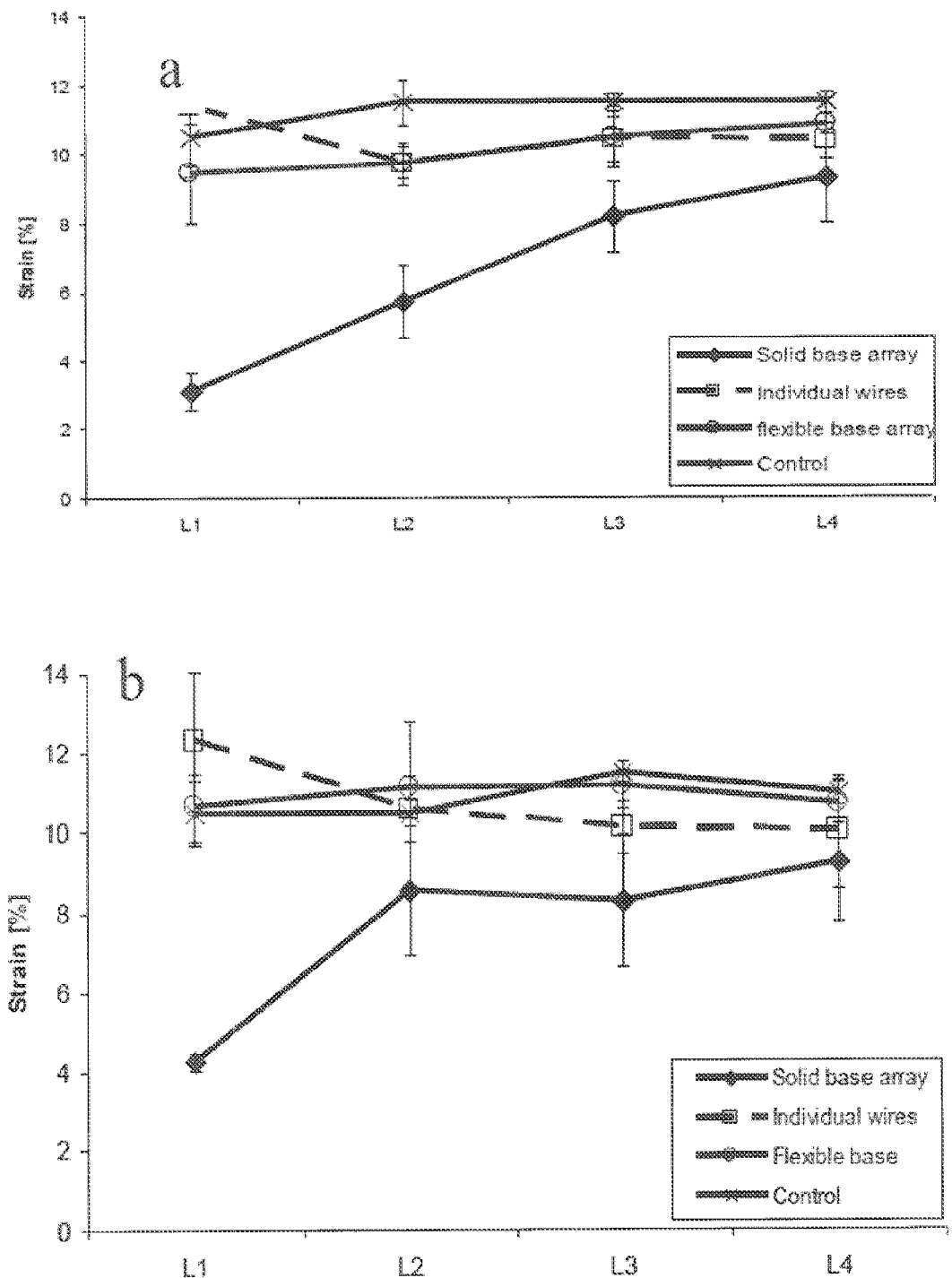
FIG. 11 provides the resulting strain on the top (11(a)) and bottom (11(b)) of candidate surrogate cord material without implant (control) or implanted with individual electrodes without a base (square), a rigid-base (diamond) or the present flexible-base electrode array (circle), when the material undergoes 12% axial tension.
Figure 13:
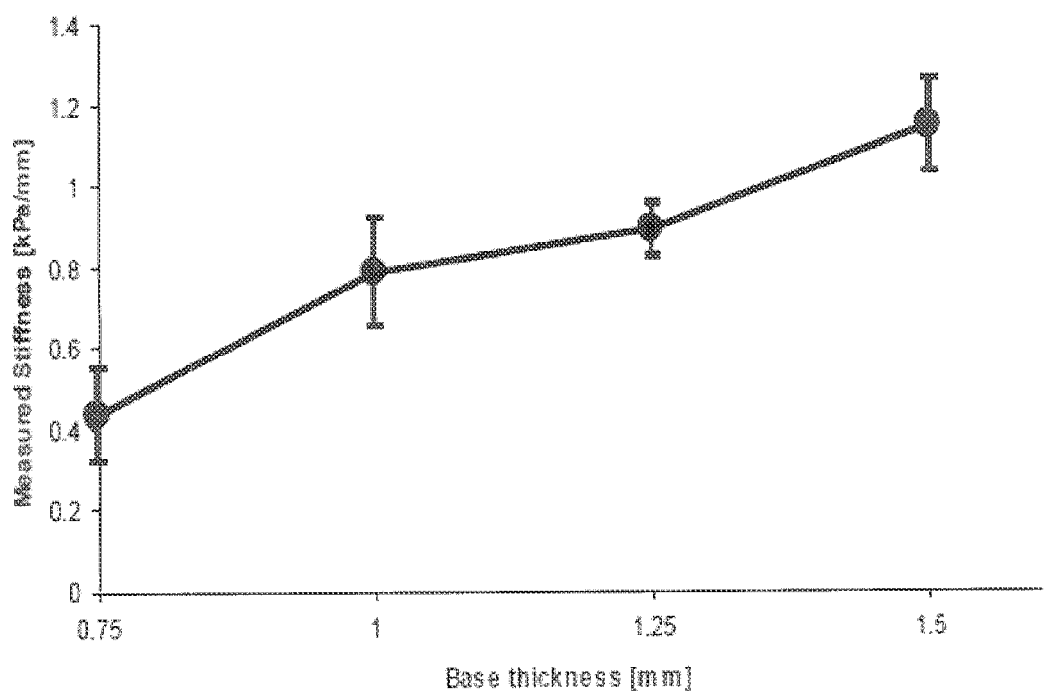
FIG. 13 shows the effect of base thickness on stiffness of the present flexible-base electrode array.
Figure 14:
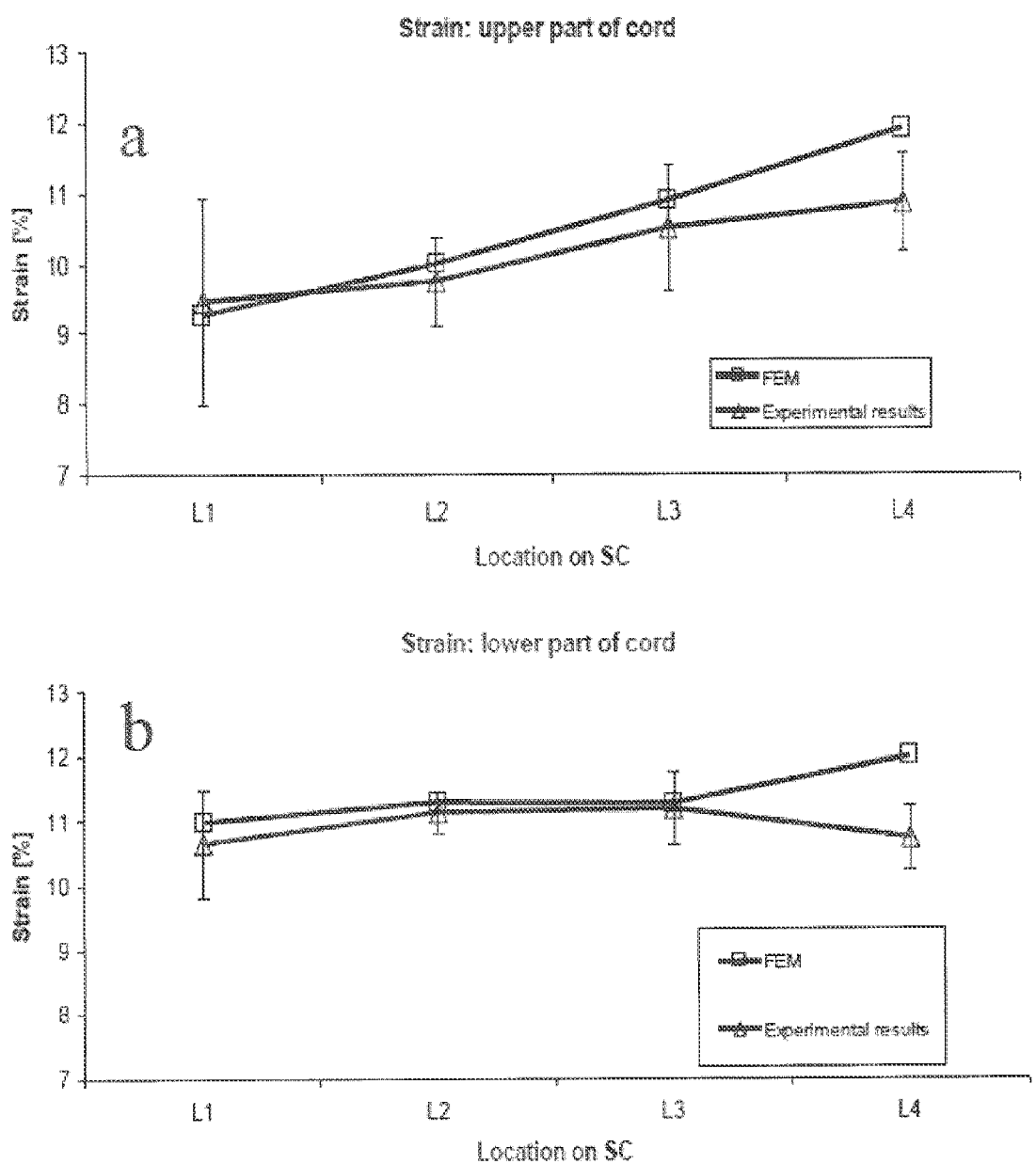
FIG. 14 shows the strain test using a finite element model (FEM) presented as a comparison between the strains measured experimentally and strains obtained from the simulations.

Results are shown in FIG. 11 and suggest that the deformation of target tissue 12 implanted with the present flexible-base electrode array 100 (circle) was similar to the deformation of target tissue 12 having no implants (control; x) and tissue 12 implanted with individual electrodes (i.e. having no base; square). More specifically, the strains measured between the reference points in the surrogate cord implanted with the FBEAs ranged between 9±1% to 12±1% which were very similar to the strain values obtained for the no-base array (9±1% to 13±1%) and control samples with no implanted wires (10±1% to 12±1%). Further, the strains measured in target tissue 12 implanted with the present array 100 were significantly different from those measured in tissue 12 implanted with rigid-based arrays (diamonds), suggesting that the rigid-base array impeded the natural deformation or movement of the target tissue 12.

Deformation (Twisting) Testing

It is desirable that the present flexible-base electrode array 100 have minimal influence on the deformation or mechanical twisting of the target tissue 12 within which it is implanted, and thus behaving similar to an implant having individual at least one electrodes 14. To evaluate the mechanical compatibility of the different electrode arrays during twisting deformation, the angle between adjacent electrodes 14 (numbered 1-8; FIG. 10(a)) was measured (e.g. using picture processing software AxioVision and done by counting pixels). Results shown in FIG. 11 show that the average rotation per unit length of the tissue 12 implanted with individual at least one electrodes 14 was 1.34±0.03°/mm, thereby within the calculated value for the deformation of the target tissue 12 alone (1.33°/mm). It was also determined that the movement of the tissue 12 implanted with the present flexible-based electrode array 100, having an average value of 1.39±0.20°/mm, was substantially similar to that tissue 12 implanted with the individual at least one electrodes 14. It is contemplated that the present flexible-base electrode array 100 may therefore move freely with the target tissue 12 within which it is implanted. This behaviour is unlike that of the target tissue 12 implanted with the rigid-base array, which was smaller at 0.004±1.16°/mm. (i.e. the rigid-base array fails to move freely with the target tissue 12 within which it is implanted). The present flexible-base electrode array 100 may provide enhanced rotation compared to known rigid-base electrode arrays.

The interaction or interfacing between the present flexible-base electrode array 100 and the target tissue 12 was also evaluated using X-ray micro-computed tomography (micro-CT), a common technique in biomedical and nanotechnology fields. The micro-CT was used to collect a series of 2D images of the wires implanted inside of the target tissue 12. All micro-CT scanning was done using a Skyscan 1076 microCT X-ray scanner (Skyscan, Kontich, Belgium), under 70 kV and 139 µA. The pixel size of the image is 17.15 µm, which allows the resolution of 18 µm. The present flexible-base array 100 was compared to target tissue 12 samples having either implants of individual electrodes (no-base) or implants of electrode arrays in which the electrodes were held together by a rigid base (e.g. the McCreery array). A pre-test scan was taken of the target tissue 12 in a relaxed position, and the tissue was then twisted by approximately 60° along its longitudinal axis. A second scan was taken to record the distance change between the at least one electrodes 14. The target tissue 12 was then twisted longitudinally such that the angle change along the length of the tissue 12 of one millimeter ($A_{mm}$) was uniform, and may be calculated using:

$$A_{mm}=60°/L \qquad (1)$$

where L is the total clamped length of the target tissue 12 (45 mm). The total expected rotation is equal to 1.33°/mm.

Stiffness

The stiffness of the present flexible-base electrode array 100 was evaluated using different base thicknesses and was measured using a DMA machine (Perkin Elmer DMA 8000, Waltham, Mass., USA). Measurements were acquired in the tension mode of the DMA machine with a strain displacement of 0.01 mm applied at a frequency of 1 Hz. All measurements were acquired at room temperature (20° C. to 25° C.) and the target dimensions of the samples were 13 mm (length)×7 mm (width)×0.3 mm (thickness). Tensile modulus of the present flexible-base electrode array 100 was calculated using the following equation:

$$K = \frac{EA}{L}$$

where K denotes stiffness in N/mm, E denotes the measured modulus of elasticity, A denotes the cross-sectional area of the sample (i.e. width×thickness), and L denotes the length of the sample measured by the DMA machine (in this case, L was a constant 6.21 mm). The results are plotted in FIG. 13.

Finite Element Modeling

The interaction between the present flexible-base electrode array 100 and its corresponding target tissue 12 was further evaluated using a two dimensional finite element model using ANSYS 11 (ANSYS Inc, Canonsburg, Pa., USA). This test was used to simulate the in vitro strain test and to calculate the stresses experienced by the target tissue 12 around the implanted array 100. For this test, the present array 100 was modelled comprising 8 electrodes (2×4; 30 µm (diameter)×4 mm (height)×1 mm (base thickness), and a modulus of elasticity of 1000 kPa (based on tensile testing results). The target tissue was modelled comprising a diameter 7.5 mm and length 40 mm, and a modulus of elasticity of 90 kPa. An eight node quadrilateral element with two degrees of freedom was used to mesh the model. The target tissue 12 and the present flexible-base electrode array 100 were assumed to operate in the elastic range and static analysis was performed. The results obtained from the model were validated against the experimental results obtained from target tissue 12 implanted with the present flexible-base electrode array 100 and rigid-based arrays. The rigid-based array was simulated by increasing the modulus of elasticity of the base in the model to 1 GPa.

The validated model was then used to study the effective (Von Mises) stresses applied by the at least one electrodes 14 on the target tissue 12. To decrease the effect of singularities at the electrode 14 tips, the stress values were measured and plotted for a region at a predetermined distance (e.g. 10 µm) away from the interfacial layer between the electrode 14 and the surrounding medium. The distance was chosen so that the obtained stresses were within the set of elements interfacing the electrodes 14 and the target tissue 12. The model assumed that the candidate target tissue 12 was isotropic, and contained no hydrostatic pressures. Simulations of implanted tissues 12 with 12% uniaxial tension (applied from one end while the other end remained fix) were then performed and the stresses induced by the electrodes 14 of the present flexible-base electrode array 10, a rigid-base, and no-base arrays were examined. Due to the symmetry of model geometry, stresses caused by the 2 outer (1 and 4) electrodes 14, were assumed to be similar; the latter also applied to the 2 inner (2 and 3) electrodes. Therefore, the stresses due to 1 outer and 1 inner electrode 14 are presented.

The calculated strains in the numerical model of the target tissue 12 implanted with the present array 100 and rigid-based arrays were plotted against the empirical measurements obtained from the physical strain model. For the target tissue 12 implanted with the present array 100, the strains calculated between L1 and L3 in the numerical model were within the standard deviations of the respective strains in the physical model (within 0.5% error). Similar results were observed for the rigid-based arrays except for the strain measured at L1 between the lower set of reference points. The difference between the two models at this location was approximately 2%. The strains calculated at L4, between the upper and lower sets of reference points, in the numerical model of the present array 100 and the rigid-based arrays had an approximate error between 1.5 and 2% from the respective strains in the physical model.

The difference in strain values at the lower L1 between the finite element model and the rigid-based may be due to errors in the optical measurements (~1% error). L1 is the distance between the inner two reference points, thus it is the smallest assessed distance and small inconsistencies in the optical measurement of the reference points produce pronounced errors.

Figure 15:
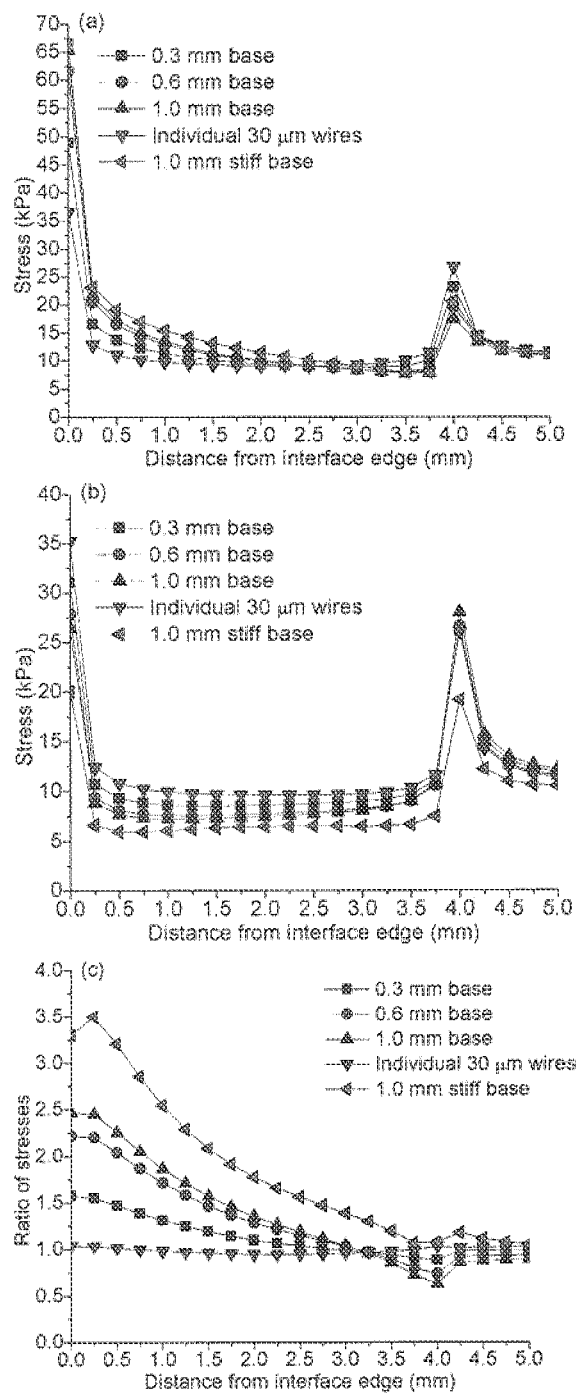
FIG. 15 shows the calculated stress induced by electrodes in the various arrays including arrays having individual electrodes, the present flexible-base array and rigid arrays.
Figure 16:
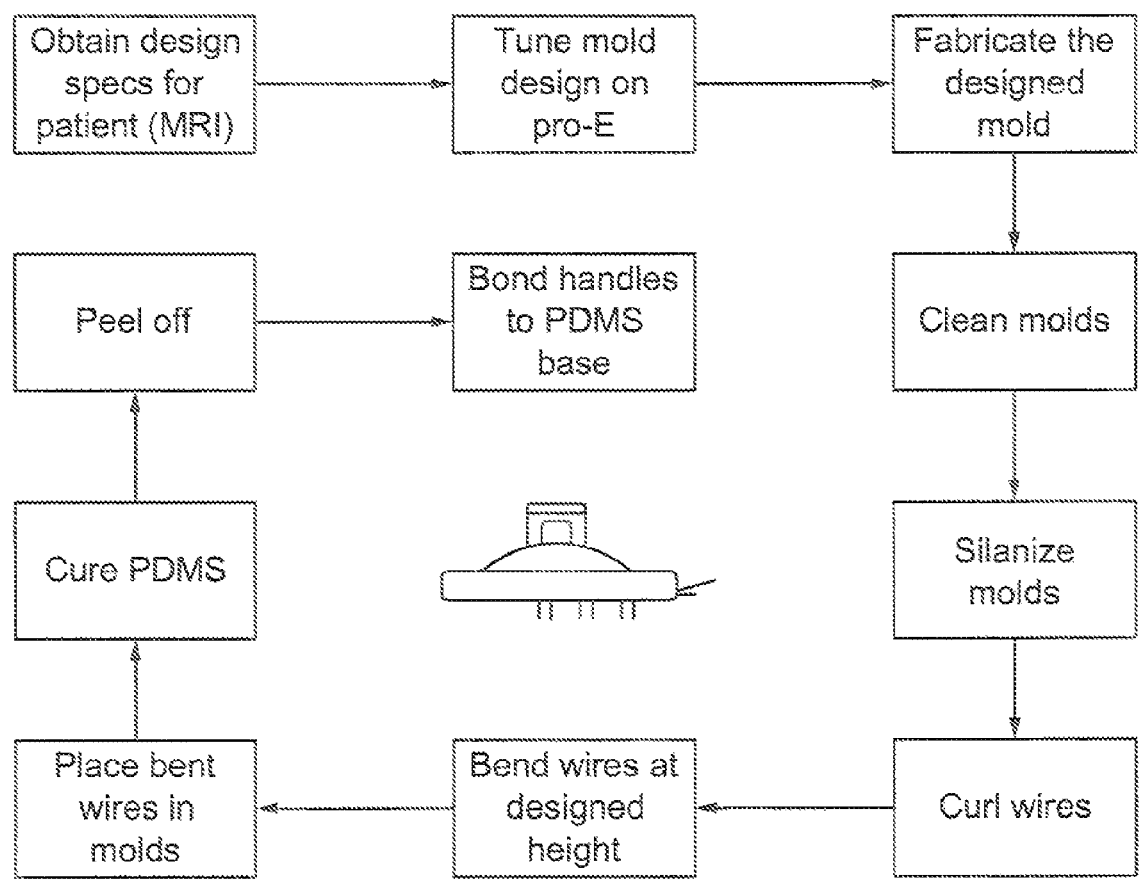
FIG. 16 provides an exemplary flow chart for manufacturing the present flexible-base electrode array.

The validated numerical model was used to calculate the stresses induced by the at least one electrode 14 of the various types of arrays on the surrounding target tissue 12. Tissue 12 implanted with individual at least one electrodes 14 were modeled by allowing the electrodes 14 to move freely with the tissue 12. This simulation was based on the assumption that no external forces are transferred to the individual electrodes 14 by the lead wires (which may be connected to a power supply). The calculated stresses induced by the electrodes 14 in the arrays with individual at least one electrode 14, the present flexible-based array 100 and the rigid-based arrays on the target tissue 12 are shown in FIG. 15. The stress induced by the electrodes 14 in all array types was highest at the interfacing edge with the target tissue 12 (distance from interfacing edge=0), decreased exponentially along the length of the electrode and increased again around the tip. The magnitude of the stresses induced by the electrodes 14 differed between the three different arrays. The stress magnitudes on the surrounding target tissue 12 induced by the outer and inner electrodes 14 in the arrays with no base were nearly identical; however, substantial differences between the stresses induced by the outer and inner electrodes 14 were seen in the present flexible-base array 100, and the rigid-based arrays.

More specifically, the outer electrodes 14 in the arrays with no base induced a stress of 41.41 kPa and 21.06 kPa at the top and tip, respectively (FIG. 15 (a)); while the inner electrodes 14 induced 39.49 kPa and 23.99 kPa at the top and tip (FIG. 15(b)). In contrast, the outer electrodes 14 in the rigid-based array induced 66.94 kPa and 27.35 kPa at the top and tip (FIG. 15(a)), and the inner electrodes 14 induced 9.81 kPa and 17.78 kPa (FIG. 15(b)). The stresses induced by the present flexible-base electrode array 10 fell in between those induced by the no base and the rigid-based array. The outer electrodes 14 induced a stress of 64.14 kPa at the top and 15.20 kPa at the tip (FIG. 15 (a)) while the inner electrodes 14 induced 29.61 kPa and 25.36 kPa at the top and tip, respectively (FIG. 15(b)).

The ratio of stresses induced by the outer to inner electrodes 14, from the surface of the target tissue 12 to 1 mm below the tip of the electrodes 14, for the various arrays was 6.82 and 1.54 at the top and tip, respectively. This ratio was 2.17 and 0.60 for the present flexible-base electrode array 100 and 1.05 and 0.88 for the no-base arrays.

Although a few embodiments have been shown and described, it will be appreciated by those skilled in the art that various changes and modifications might be made without departing from the scope of the invention. The terms and expressions used in the preceding specification have been used herein as terms of description and not of limitation, and there is no intention in the use of such terms and expressions of excluding equivalents of the features shown and described or portions thereof, it being recognized that the invention is defined and limited only by the claims that follow.

We claim:

1. An electrode array for implantation in a target neural tissue, the array comprising:
   a flexible biocompatible elastomer base having a modulus of elasticity of up to approximately 150 MPa; and
   at least one microwire electrode protruding from the base, for implantation into and biocompatible with the target neural tissue;
      wherein the base interfaces with the surface of the target neural tissue and the electrodes penetrate into the target neural tissue.

2. The array of claim 1, wherein the base comprises a plurality of rows having at least one electrode.

3. The array of claim 2, wherein the base comprises two rows of at least one electrode.

4. The array of claim 1, wherein the flexibility of the base is equal to or greater than the target neural tissue.

5. The array of claim 1, wherein the base is made of polydimethylsiloxane (PDMS).

6. The array of claim 1, wherein the base is made of silicone elastomer.

7. The array of claim 6, wherein the silicone elastomer is MED 6215.

8. The array of claim 1, wherein the base further comprises a temporary handle.

9. The array of claim 1, wherein the target tissue is brain or spinal cord.

10. A method of fabricating the flexible-base electrode array of claim 1.

11. A method of implementing the flexible-base electrode array disclosed in claim 1 comprising stimulating or recording electrical activity in the target tissue.

12. The method of claim 11, wherein the target tissue is brain, spinal cord or nerve.

13. The method of claim 11, for intraspinal microstimulation.

14. The method of claim 13, wherein the use is long term.

15. The array of claim 1, wherein the modulus of elasticity is at least less than or equal to the target neural tissue.

16. "A method of implanting an electrode array into target neural tissue, comprising:
   a) penetrating at least one microwire electrode of the electrode array into the target neural tissue;
   and b) interfacing a flexible biocompatible elastomer base from which the at least one microwire electrode protrudes with a surface of the target neural tissue".

17. The method of claim 16, further including:
   stimulating and recording electrical activity in the target neural tissue with the electrode array.

18. The array of claim 1, wherein the entire portion of the microwire protruding from the base penetrates into, and is in direct contact with, the target neural tissue.

19. An electrode array for implantation in a target neural tissue, the array comprising:
    a flexible biocompatible elastomer base having a modulus of elasticity of up to approximately 150 MPa; and
    at least one multi-contact cylindrical electrode protruding from the base, for implantation into and biocompatible with, the target neural tissue;
    wherein the base interfaces with the surface of the target neural tissue and the electrodes penetrate into the target neural tissue.

* * * * *

UNITED STATES PATENT AND TRADEMARK OFFICE
CERTIFICATE OF CORRECTION

PATENT NO.        : 9,433,787 B2
APPLICATION NO.   : 13/657552
DATED             : September 6, 2016
INVENTOR(S)       : Elias et al.

It is certified that error appears in the above-identified patent and that said Letters Patent is hereby corrected as shown below:

In the Claims

Column 18, Line 58, in between "16." and "A" delete "."

Column 18, Line 64, in between "tissue" and "." delete "."

Signed and Sealed this
Twenty-seventh Day of June, 2017

Joseph Matal
*Performing the Functions and Duties of the*
*Under Secretary of Commerce for Intellectual Property and*
*Director of the United States Patent and Trademark Office*